(12) United States Patent
Schaffner et al.

(10) Patent No.: US 11,571,304 B2
(45) Date of Patent: Feb. 7, 2023

(54) MEDICAL IMPLANT AND METHOD FOR HEART VALVE REPAIR

(71) Applicant: CoreMedic AG, Biel (CH)

(72) Inventors: Silvio Schaffner, Berlingen (CH); Tobias Aeschlimann, Burgdorf (CH); Oliver Wüthrich, Herrenschwanden (CH); Thomas Bauer, Allensbach (DE)

(73) Assignee: COREMEDIC AG, Biel (CH)

( * ) Notice: Subject to any disclaimer, the term of this patent is extended or adjusted under 35 U.S.C. 154(b) by 320 days.

(21) Appl. No.: 17/034,670

(22) Filed: Sep. 28, 2020

(65) Prior Publication Data

US 2021/0022866 A1    Jan. 28, 2021

Related U.S. Application Data

(62) Division of application No. 15/768,883, filed as application No. PCT/CH2016/000136 on Oct. 19, 2016, now Pat. No. 10,806,578.

(30) Foreign Application Priority Data

Oct. 21, 2015    (CH) ..................................... 01533/15

(51) Int. Cl.
  *A61F 2/24*    (2006.01)
  *A61B 17/04*    (2006.01)

(52) U.S. Cl.
  CPC ........ *A61F 2/2457* (2013.01); *A61B 17/0401* (2013.01); *A61F 2/2466* (2013.01);
  (Continued)

(58) Field of Classification Search
  CPC .. A61F 2/2457; A61F 2/2466; A61B 17/0401; A61B 2017/0409;
  (Continued)

(56) References Cited

U.S. PATENT DOCUMENTS

2007/0118151 A1    5/2007  Davidson
2011/0011917 A1    1/2011  Loulmet
(Continued)

FOREIGN PATENT DOCUMENTS

WO    2012/040865    4/2012

OTHER PUBLICATIONS

International Preliminary Report on Patentability dated Apr. 24, 2018 (dated Apr. 24, 2018), Application No. PCT/CH2016/000136, 8 pages.

*Primary Examiner* — Suba Ganesan
(74) *Attorney, Agent, or Firm* — Rankin, Hill & Clark LLP

(57) ABSTRACT

A sutureless implant for replacing damaged natural chordae tendineae of a human or possibly animal heart, the implant including a distal implant part, a proximal implant part, and an artificial chord. The distal implant part is configured to fit in a lumen of an implant delivery device and includes a self-spreading portion spreading radially outside when the distal implant part is released from the lumen, the self-spreading portion being capable of anchoring the distal implant part in human muscle tissue. The proximal implant part is configured to fit in the lumen of the implant delivery device and comprises a self-spreading portion spreading radially outside when the proximal implant part is released from the lumen, the self-spreading portion being capable of bearing on a tissue portion of leaflet tissue. The distal implant part and the proximal implant part are connected by the chord.

17 Claims, 2 Drawing Sheets

(52) U.S. Cl.
CPC ............... *A61B 2017/0409* (2013.01); *A61B 2017/0417* (2013.01); *A61B 2017/0437* (2013.01); *A61B 2017/0458* (2013.01); *A61B 2017/0464* (2013.01)

(58) Field of Classification Search
CPC .... A61B 2017/0417; A61B 2017/0437; A61B 2017/0458; A61B 2017/0464
See application file for complete search history.

(56) References Cited

U.S. PATENT DOCUMENTS

| | | |
|---|---|---|
| 2012/0035712 A1 | 2/2012 | Maisano et al. |
| 2013/0096672 A1* | 4/2013 | Reich .................... A61F 2/2457 623/2.11 |
| 2014/0243968 A1 | 8/2014 | Padala |
| 2017/0252032 A1* | 9/2017 | Hiorth .................... A61F 2/2466 |

* cited by examiner

MEDICAL IMPLANT AND METHOD FOR HEART VALVE REPAIR

BACKGROUND OF THE INVENTION

Field of the Invention

The invention is in the field of surgical, for example minimally invasive or interventional cardiology, devices for heart valve repair. It more particularly relates to an implant for repairing an atrioventricular heart valve, in particular the mitral heart valve or also the tricuspid heart valve, and to an according method.

Description of Related Art

Prolapses of a leaflet of the mitral valve into the left atrium and resulting valve insufficiency can cause serious dysfunctions of the heart. One reason for such prolapse is a damaging of the tendons (chordae tendineae) that connect the leaflets of the mitral valve to the papillary muscle through the left ventricle. Such damage may for example be a result of a myocardial infarction, tissue degeneration or infectious disease.

A repair of such a prolapse demands the leaflet or leaflets to be re-connected to the papillary muscle, for example by synthetic fibres, such as Gore-tex® fibres. Such an approach in accordance with the state of the art demands suturing the implant to a papillary muscle. A first disadvantage of such a repair process is that it is only possible while the heart is inactive, thus the surgical repair demands that the heart is stopped and drained of blood, while a cardiopulmonary bypass is used. It has also been described that it is possible to attach the suture to and through the apex of the heart, however, as also described, results are not as good as if sutures are attached to the papillary muscles, which is the physiologic site. A second disadvantage is that the success of the operation depends strongly on the skill of the surgeon, especially in terms of length adjustment and time invested while the heart is arrested. A further disadvantage is that the fibres sutured to the leaflet may cause long-time damage.

In WO 2012/040865, approaches are presented according to which a distal anchor attached to a filament serving as artificial chord is used that can be shot across the left ventricle. Also tools for fixing an artificial chord to the leaflet and tools for temporary fixation of the leaflet of the beating heart are illustrated.

US 2011/0011917 describes methods and devices for cardiac valve repair. The devices may include a dart anchor with self-expandable legs for being secured into cardiac tissue and a staple to be deployed into tissue of the leaflet, which staple may be secured to a tensile member that is also connected to the dart anchor. A pledged may be used to spread loads, i.e. to prevent the leaflet tissue from being injured by the staple. US 2011/0011917 also discloses an anchor with an eyelet in which a chord can slide. This anchor is to be attached to a leaflet.

SUMMARY OF THE INVENTION

It is an object of the present invention to provide an implant for repairing an atrioventricular, in particular the mitral or also the tricuspid, heart valve, and an according method, which implant and method overcome drawbacks of prior art devices and methods and which are easy to implant, suited also for interventional surgery and provide a reliable and well tissue-compliant repair.

According to an aspect of the invention, an implant is provided, the implant being a sutureless implant for replacing damaged natural chordae tendineae of a human or possibly animal heart, the implant including a distal implant part, a proximal implant part and an artificial chord, wherein the distal implant part is configured to fit in a lumen of an implant delivery device and includes a self-spreading portion spreading radially outside when the distal implant part is released from the lumen, the self-spreading portion being capable of anchoring the distal implant part in human tissue, especially muscle tissue;

wherein the proximal implant part is configured to fit in the lumen of the implant delivery device and includes a self-spreading portion spreading radially outside when the proximal implant part is released from the lumen, the self-spreading portion being capable of bearing on a tissue portion of leaflet tissue, and wherein the distal implant part and the proximal implant part are connected by the chord.

The lumen into which the implant parts fit in a non-spread state is tube-shaped and may be a lumen of a bendable tube of a minimally invasive surgical apparatus (such as a catheter) or of another surgical instrument such as a needle. An interior diameter of the lumen may be at most 2 mm or at most 1.5 mm, especially at most 1.2 mm, for example 1 mm or possibly less. After spreading, the respective implant parts are more bulky, thus, the distal implant part or the proximal implant part or both have dimensions that cause them not to fit into the lumen any more without being deformed into a de-spread state.

The implant parts may be designed so that they may rest one next to the other for being released sequentially. For example, the instrument (catheter, other instrument) may first be advanced to the tissue in or into which the distal implant part is to be released. After release of the distal implant part, the instrument may be moved to the leaflet, where the proximal implant part is released.

The distal implant part may include a shaft portion extending proximally from a distal head and a plurality of implant legs that in the non-released state lie against the shaft portion also projecting proximally (backward) from the distal head and in the implanted state project to the proximal side and may be bent radially outward away from the shaft portion. The chord is attached to the proximal end of the shaft portion or is guided in the shaft portion and is attached to a distal portion of the shaft portion. By this, the orientation of the distal implant part once it is implanted is stabilized: when the chord is pulled, the anchor is forced into its desired orientation, thus the shaft portion has a stabilizing effect: the orientation of the distal implant is automatically aligned with the direction of the pulling forces acting on the implant.

The number of legs may be an even number. This has the advantage that every leg has a well-defined counterpart, and this results in a balanced configuration. In an embodiment, the number is at least four, or at least six, especially six. It has been found that six legs may provide an especially stable anchoring. As an alternative to an even number, the distal anchor may have an odd number of legs.

The chord may be fastened to the distal implant part in a manner that it is knotless at least at the proximal end. For example, it may be fastened to the distal end (by a knot, by crimping, welding, soldering, gluing and/or another technique) and guided axially through the distal implant part, thus through the shaft portion if applicable.

In some embodiments, the legs are sharpened. To this end, they are for example provided, at their outer (especially proximally-outwardly facing) ends, with at least one facet that is at a non-perpendicular angle to their axis. Especially, in embodiments, between two facets a radially-outwardly facing edge may be formed that eases penetration of the respective leg into surrounding tissue when the legs are released. In addition or as an alternative, the sharpening of the legs may form a tip at the legs' outer ends that when the legs are released and bent outwardly faces radially-outwardly.

The legs may be self-expandable, so that in a released state the legs project from the shaft portion to be bent away therefrom by the effect of an elastic force, especially due to superelasticity. To this end, the material of the distal implant part or at least of a portion thereof may be of a shape memory material.

In addition or as an alternative, the ends of the legs of the distal implant part may be shaped in a way that the legs are being stretched further away from the shaft in case a pulling force is applied. The may lead to an improved anchoring in the tissue. Thus, in this concept it is a barb-like effect that contributes to the anchoring of the distal implant part in the tissue.

A result of this optional feature is that there is a reduced tendency of the distal implant part to cut into the muscle tissue when subject to pulling forces.

The legs may be of equal lengths. In special embodiments, the legs may have different lengths. Especially, the distal implant part may have at least one leg of a first length and at least one leg of a second, different length. A combination of short and long legs may add to the anchoring strength in that anchoring takes place in different depths within the muscle.

The distal implant part may in embodiments have a blunt distal end, i.e. be shaped so that it does not itself have the capability of piercing through muscle tissue. In these embodiments, the instrument from which the distal implant part (and in many embodiments also the proximal implant part) is released is piercing, for example a needle. Embodiments in which the distal implant part has a blunt distal end feature the advantage that damage to muscle tissue arising from the distal implant part advancing further into tissue after the operation can be excluded or at least made improbable.

In embodiments, the implant may be composed of a shaft piece forming a shaft portion and a crown piece with the legs. Such a shaft piece may form a distal collar. The crown piece may be mounted surrounding the shaft piece and possibly, if applicable, abutting distally against the collar, so that a distal end of the crown piece and the collar together constitute a head of the above-described kind.

The distal implant part may be of a suitable material that has the necessary elastic properties for the self-spreading portion (such as the legs) to spread when released. It may especially be made of a shape memory material having superelastic properties, such as Nitinol or another shape memory metal or of a shape memory plastic. In embodiments where the distal implant part has several pieces, such as a shaft piece and a crown piece, at least the portion (such as the crown piece) that has the legs may be of a shape memory material.

In addition to a shaft portion and the legs, the distal implant part may further include a proximal collet piece. This collet piece may in the non-released state be arranged proximally of the proximal ends of the legs and have a radial extension that approximately corresponds to the radial extension of the legs in the non-released state or be higher than the latter. Thereby it has the effect of protecting the parts during mounting of the implant from the (relatively sharp, due to the reduced dimensions) legs, especially of protecting the chord. Also, during implantation it may contribute to defining an orientation of the implant and thereby ensure proper release.

The proximal implant part in contrast to prior art approaches may be configured to lie flat on a surface of the leaflet tissue, with the chord extending from the proximal implant part through the leaflet tissue and through the ventricle to the proximal implant part. To this end, the proximal implant part may, for example, include a flattish distally-facing abutment surface (distally-facing in the implanted state, i.e. facing to the side to which the chord runs). This is in contrast to prior art approaches that teach to clamp the leaflet by a leaflet anchor or to other prior art approaches that teach to suture the leaflet.

Especially, the proximal implant part may be configured to only lie on the leaflet and to thereby being secured to it—without the proximal implant part having any fastening mechanism that extends within the leaflet or through the leaflet.

The proximal implant part may hold to the leaflet without any additional fastening mechanism (such as a suture) or artificial fastening means, only by the design of the implant as such that includes the distally facing abutment surface lying on the leaflet tissue—especially by the chord extending through the leaflet tissue and the ventricle to the distal implant part, possibly assisted by a distally-facing structure on the abutment surface that includes portions that protrude into the tissue, without penetrating through it, and/or is indented with respect to it, to prevent shifting movements.

The proximal implant part especially will, after implantation, be placed on one side of the leaflet only and not for example extend through the leaflet. The side on which the proximal implant part lies on the leaflet tissue is the atrium-facing upper side of the leaflet.

Especially, the proximal implant part is free of any clamping mechanism and does not include any portion that bears against the ventricle-facing lower surface of the leaflet.

As such, the proximal implant part is capable of coupling distally facing forces (forces towards the side of the ventricle) into the leaflet but its structure would not allow to couple proximally-facing forces into the leaflet (the proximal implant part cannot pull the leaflet towards the atrium side) and vice versa. The proximal implant part may have a central body and a plurality of arms that lie against each other or against a shaft portion in the non-released state and are bent radially outward in the released state. The central body and the outwardly extending arms together form an abutment surface. In the released state the proximal implant part may lie flat on the leaflet surface.

In an embodiment, the proximal implant part, and especially the arms thereof, comprises/include an optional protrusion (hook/piercing protrusion or other structure) at the abutment surface. Such a hook may assure that there is no relative movement of the proximal implant part and the leaflet tissue surface once implantation has been carried out. This may foster the necessary ingrowth. If the structure includes a protrusion, a piercing depth of such protrusion will in many embodiments be smaller than a thickness of the leaflet.

The proximal implant part may be of a suitable material that has the necessary elastic, for example super-elastic properties for the self-spreading portion (such as the arms) to spread when released. It may especially be made of a shape memory material, such as Nitinol or another shape memory metal or of a shape memory plastic.

Alternative materials for the distal and/or proximal implant part are polymer-based materials (plastics), such as PEEK. A special class of materials is resorbable (biodegradable) materials, such as polylactide polymers or biodegradable alloys, for example biodegradable magnesium or iron alloys. The principle of applying a bioresorbable implant part relies on the fact that during the time of resorption, the tissue will grow to integrate the chord, whereby after a certain time the implant part(s) will not be required any more.

More in general, any suitable material that is biocompatible and preferably radiopaque can be used.

The attachment of the chord to the proximal implant part may be knotless. In an embodiment, the proximal implant part is shaped so that the chord is doubled by being guided from the distal implant part through the proximal implant part and back to the distal implant part. Especially, the proximal implant part may include two openings through which the chord is guided from the distal to the proximal side and back to the distal side. Especially, the openings may be located centrally with respect both, to lateral and to axial directions so that when the chord is pulled the force is evenly distributed over the abutment surface and there is no tilting momentum (no torque) when the proximal implant part is being pulled.

In an alternative group of embodiments, the attachment of the chord to the distal implant part may be knotless, with the chord being doubled by being guided from the proximal implant part through the distal implant part and back to the proximal implant part. To this end, the distal implant part may for example include a horizontal through opening through the shaft portion through which the chord is guided.

Generally, the chord may be coupled to the proximal implant part in a manner that a pulling force on the chord does not transmit any torque on the proximal implant part lying flat on the leaflet.

In embodiments with a single chord portion running between the proximal and distal implant parts, this may be achieved by placing the location of attachment of the chord in a center of area of with respect to the abutment surface.

In embodiments with a plurality of chord portions running between the proximal and distal implant parts, this may be achieved by placing the center between the locations of attachment of the chord (for example the through openings through which the chord runs) at the location of the center of area with respect to the abutment surface.

An optional additional knot (especially with a diameter greater than the openings though which the chord runs) of the chord between the proximal and distal implant parts may define a length of the distance between the proximal and distal implant parts.

In both, embodiments with a single chord portion and embodiments with a plurality of chord portions, it is also possible to provide a displaceable know that allows for an in-situ adjustment of the maximum distance between the distal and proximal implant parts.

Also, in this embodiment and in other embodiments the chord may be mounted displaceably with respect to the proximal implant part. In embodiments in which the chord has a fixed length, this allows to store the chord proximally of the proximal implant part in the instrument. This is also an option in embodiments with only one chord portion running between the distal and proximal implant parts, namely if the chord runs through a (for example centrally located) opening of the proximal implant part, with a knot proximally of the opening.

In embodiments in which the chord is not displaceable with respect to the proximal implant part, it may be attached to the proximal implant part by a knot, by crimping or welding or clamping or other fastening technique.

Generally, the chord may have a fixed, defined chord length, or may have an adjustable chord length. If the chord length is adjustable, the connection of the chord to the proximal implant part may be performed by the surgeon, for example by knotting.

In cross section, the proximal implant part in a non-released state may have the shape of a circular segment, for example with a central angle of around 180° or more than 180°. Especially, such a central angle may be at least 120° or at least 90°.

The present invention also concerns a distal implant part with the according properties discussed and claimed in the present text and a proximal implant part with the according properties discussed and claimed in the present text—thus the herein described and claimed distal and proximal implant parts each may be used together with other implant parts or for example in combination with suturing, etc.

The invention further concerns a method of implanting an implant of the kind described and claimed in this text, the method including piercing a leaflet of the heart tissue, advancing a tube containing the proximal and distal implant parts through the pierced leaflet and through the heart's ventricle, releasing the distal implant part into tissue, especially muscle tissue of the ventricle, retracting the tube to the leaflet, releasing the proximal implant part proximally of the leaflet, and retracting the tube.

In embodiments, the tissue into which the distal implant part is released is the muscle tissue of the papillary muscle.

This method can be carried out in a minimally invasive or interventional manner, on a beating heart, with the tube (that may have a distal tip to be a needle) inserted through a system of catheters. Alternatively, the method may be carried out by conventional surgery of the open, non-beating heart.

BRIEF DESCRIPTION OF THE DRAWINGS

Hereinafter, principles and embodiments of the invention are described referring to drawings. In the drawings, same reference numbers refer to same or analogous elements. The drawings show.

DETAILED DESCRIPTION OF THE INVENTION

Figure 1:
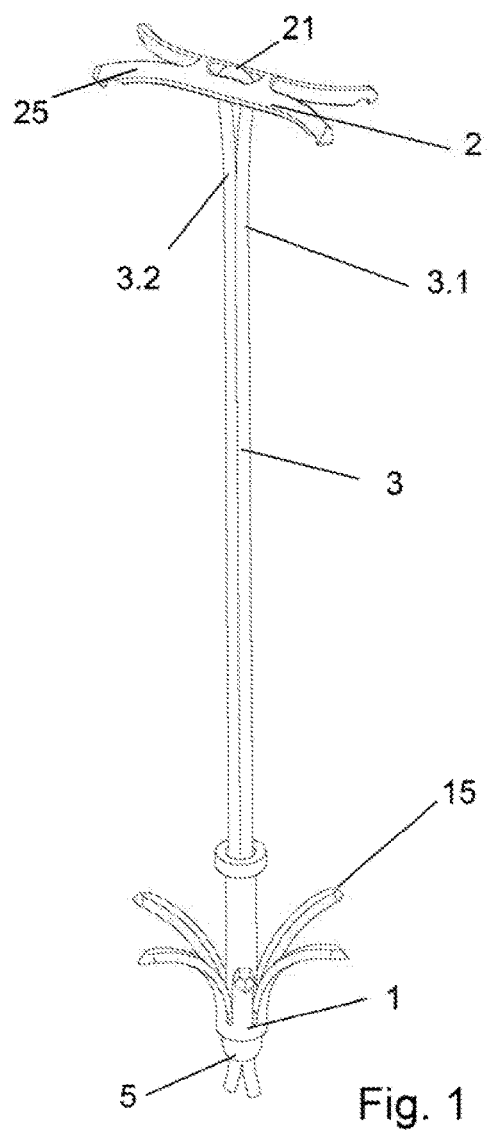
FIG. 1 an implant.

The implant illustrated in FIG. 1 includes a distal implant part 1, a proximal implant part 2 and a chord 3 connecting the proximal and distal implant parts. The chord 3 is guided from a distal end of the distal implant part 1 to the proximal implant part 2 and through the proximal implant part 2 back to the distal end of the distal implant part 2, so that the chord 3 is doubled and has two chord portions 3.1, 3.2 between the proximal and distal implant parts. Within the distal implant part 1 and between the distal and proximal ends thereof, the chord portions 3.1, 3.2 are guided in a shaft 13, and they are secured by a knot 5 distally of the distal implant part 1.

Figure 2:
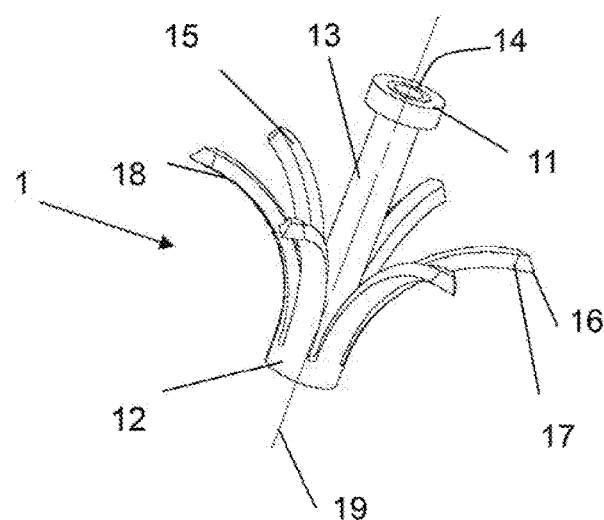
FIG. 2 a distal implant part.
Figure 3:
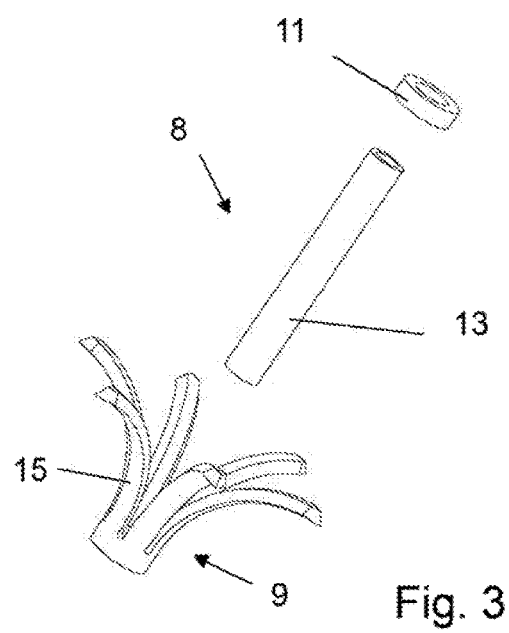
FIG. 3 an exploded view of elements of the distal implant part of FIG. 2.

In FIGS. 2 and 3, the distal implant part 1 is shown in somewhat more detail. In the depicted embodiment, it is composed of a shaft piece 8 and a crown piece 9 as well as an optional collet piece 11. The shaft piece 8 acts as a stabilizer that helps orientating the distal implant part 1 in a longitudinal manner, aligned and with the proximal end pointing towards the leaflet. It includes is a tube-like shaft 13 with a longitudinal through opening 14 through which the chord 3 on is passed. At the distal end, the shaft piece 8 may optionally further include a collar (not shown) around the shaft. The crown piece 9 is placed on/around the shaft 13 and is designed to fulfill, together with the shaft piece 8 the anchor function. To this end, the crown piece includes, attached to a distal head portion 12, a plurality of backwardly (proximally) protruding legs 15 that, after release of the distal implant part, spread against and inside the tissue of the papillary muscle.

The collet piece 11 is mounted at the proximal end of the shaft and in the depicted embodiment is initially a separate piece. Alternatively, it would be possible to provide a collet directly on the shaft and one-piece with it.

The (proximodistal) axis 19 is also illustrated in the Figure.

The distal implant part 1, or at least the crown piece thereof, may optionally be made of a shape memory material, such as a shape memory metal, for example Nitinol.

In contrast to the depicted embodiment, the distal implant part may be one piece with the legs being firmly attached to the rest of the distal implant part.

In the depicted embodiment, the legs of the distal implant part are pointed at the outermost surface. More in particular, the legs are each provided with a plurality of facets 17 that meet at edges, wherein there is at least one edge 18 and/or a tip 16 that faces outwardly and helps easing penetration into the tissue.

Figure 4:
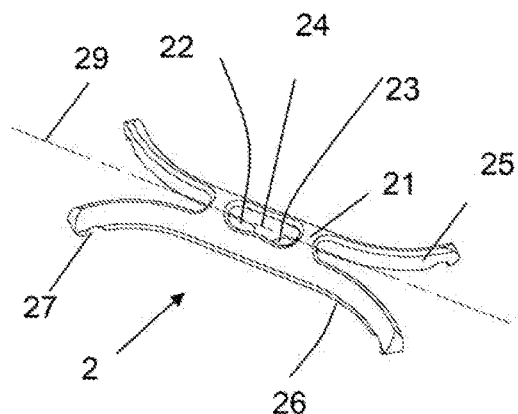
FIG. 4 a proximal implant part.

FIG. 4 depicts the proximal implant part 2. The proximal implant part is elongate defining a longitudinal axis 29. It has a central body 21 and four arms 25 one-piece with the central body and extending outwardly from the central body.

The lower side of the central body and the arms forms an abutment surface that rests against the leaflet tissue after implantation.

The chord 3 mechanically couples the proximal implant part 2 and the distal anchor part 1 with each other and defines a maximum distance between these implant parts. To this end, the proximal implant part has a first chord opening 22 and a second chord opening 23 separated by a bridge 24. The chord runs through the first chord opening, over the bridge and back to the second chord opening so that it is looped through the proximal implant part. The bridge 24 has rounded features so that the chord can slide along it easily without being damaged. The first and second openings are positioned so that the center of the abutment area is in the middle between them.

As a consequence, if a force tries to pull away the proximal implant part 2 from the distal implant part 1, the chord 3 couples a counter force into the proximal implant part, which counter force acts on the center of area of the proximal implant part abutment surface, at least with respect to longitudinal directions. Because the openings 22, 23 lie on the axis 29, the counter force also acts on the center with respect to lateral directions.

As a consequence, a pulling by the chord acting on the proximal implant part will not cause any torque on the proximal implant part.

While in the depicted configuration the chord 3 is doubled and looped through the proximal implant part, this effect could for example also be achieved if the chord was one-way only and attached to a spot of the center of area or runs through a single opening in the center of area.

The arms 25 of the proximal implant part 2 are bent outwardly away from the axis. Thereby, the proximal implant part is better supported by the leaflet tissue. On the abutment surface, the arms each include an optional hook feature 27.

In embodiments, the central body may further have, close to the transition to the arms 25,h shallow lateral recesses (not shown) that cause a waist to make the proximal implant part more flexible to the outward bending of the arms.

Figure 5:
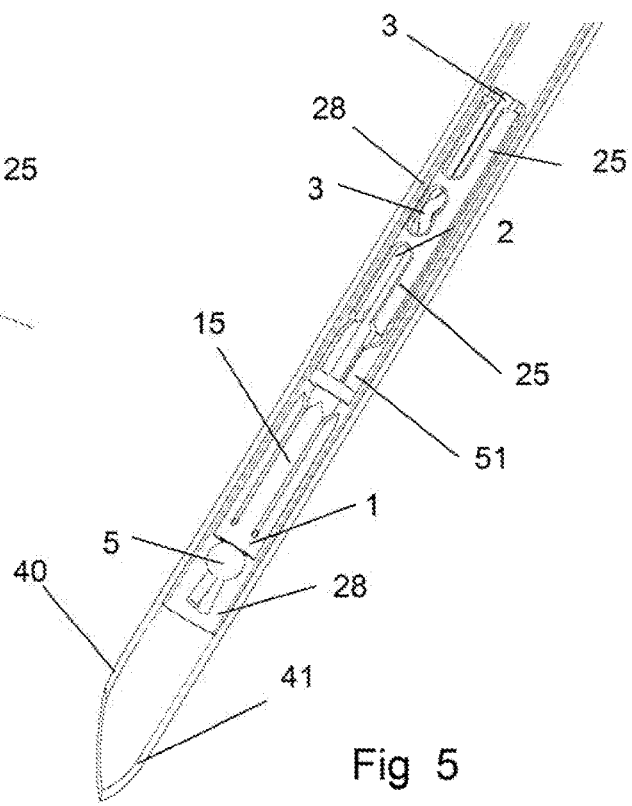
FIG. 5 a cannulated needle forming, in its interior, the lumen, with the implant before the implant is released from the lumen.

FIG. 5 shows the implant prior to its release from the lumen from which it is implanted. The lumen is constituted by a hollow tube 40 that has a distal tip 41 and is thus a cannulated needle. An inner diameter of the hollow tube is 1 mm.

The distal implant part 1 and the proximal implant part 2 are both arranged inside the tube 40. In the figure, the tube 40 is shown transparent so that the elements inside it are visible in the figure. The tube 40, in addition to the distal and proximal implant parts, also contains the chord 3 that runs from the distal implant part 1 through the openings 22, 23 and forms a loop proximally of the proximal implant part.

Further, the system includes an anchor carrier 51. The anchor carrier reaches from proximally of the proximal implant part 2 to distally of the proximal implant part. It forms a seat for the proximal implant part, defines its orientation in the tube and secures the proximal implant part against escaping to distal directions.

The system includes a pushing mechanism for moving the anchor carrier and the implant parts relative to the tube at least into distal directions (this includes the possibility of retracting the tube into a proximal direction while holding the parts still with respect to the tissue). Such a pushing mechanism may be flexible to bending movements but will be capable of transmitting axial forces. Such a pusher may optionally be one-piece with the anchor carrier, i.e. the most distal portion of such a pusher may be the anchor carrier or may be constituted by a separate piece proximally of the anchor carrier; then optionally the anchor carrier may be fastened to the pusher so that anchor carrier may be retracted into the tube by pulling the pusher after the proximal implant part has been released.

In the depicted embodiment, the system further includes a sleeve 28 inside the tube 40, the sleeve encompassing the anchor carrier and the implant prior to the implant's release. The purpose of such an optional sleeve is to protect the implant parts (including the chord) from the needle-like tip distal tip 41 of the tube and also to reduce the risk of injuries of the heart tissue.

Figure 6:
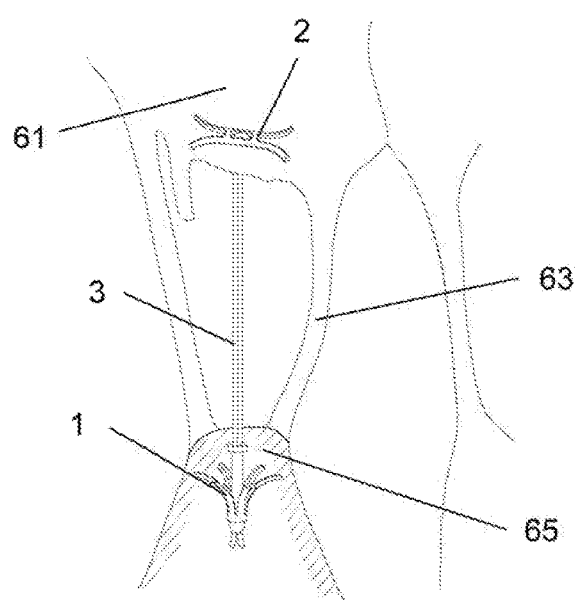
FIG. 6 the implant implanted after operation.

FIG. 6 shows the distal implant part 1 anchored in the papillary muscle. The artificial chord 3 runs through the ventricle and through an opening of the leaflet; the proximal implant part is placed on the proximal side of the leaflet 61, with the abutment surface resting on the leaflet tissue. By this, the implant assists the natural chordae 63 if they are damaged or otherwise not sufficient for the mitral valve to close sufficiently.

What is claimed is:

1. An implant for replacing or supplementing damaged natural chordae tendineae of a human or animal heart, the implant comprising a distal implant part, a proximal implant part and an artificial or allograft or xenograft chord, wherein the distal implant part is configured to fit in a lumen of an implant delivery device and comprises a self-spreading portion spreading radially outside when the distal implant part is released from the lumen, the self-spreading portion being capable of anchoring the distal implant part in tissue;

wherein the proximal implant part is configured to fit in the lumen of the implant delivery device and comprises a self-spreading portion spreading radially outside when the proximal implant part is released from the lumen, the proximal implant part being capable of bearing on a tissue portion of leaflet tissue, and wherein the distal implant part and the proximal implant part are connected by the chord, the chord being looped through the proximal implant part by extending from the distal implant part through a first opening of the proximal implant part and a second opening of the proximal implant part back to the distal implant part, and the chord being displaceable relative to the proximal implant part by a sliding movement that centers the proximal implant part relative to the chord when the proximal implant part implant is subject to a pulling force relative to the distal implant part.

2. The implant according to claim 1, wherein the proximal implant part has an abutment area configured to lie on the tissue portion of the leaflet tissue, and wherein a middle point between the first and second openings coincides with a center of the abutment area.

3. The implant according to claim 1, wherein the distal implant part comprises a shaft portion and a plurality of legs that in a non-released state lie against the shaft portion, wherein the shaft portion and the legs both extend proximally from a distal head, wherein in a released state the legs are bent radially outwardly away from the shaft portion, and wherein two ends of the chord each run through the shaft portion from a proximal portion thereof to a distal portion thereof and are fixed relative to the distal portion.

4. The implant according to claim 1, wherein the proximal implant part has a central body and a plurality of arms integral with the central body, the arms extending outwardly from the central body, wherein the first and second openings are openings in the central body.

5. The implant according to claim 4, wherein pairs of the arms extend outwardly from the central body on each of two opposite ends of the central body.

6. The implant according to claim 1, wherein the first and second openings are separated by a bridge.

7. The implant according to claim 6, wherein a proximal surface of the bridge is offset with respect to an outer surface of the proximal implant part, whereby between the first and second openings a groove for the chord is formed.

8. The implant according to claim 6, wherein the bridge has rounded openings.

9. A medical device, comprising:
an implant for replacing or supplementing damaged natural chordae tendineae of a human or animal heart; and
an implant delivery device;
the implant delivery device comprising:
a hollow tube constituting a lumen and defining a proximodistal axis,
the implant comprising:
a distal implant part configured to be anchored in tissue,
a proximal implant part configured to bear on a tissue portion of leaflet tissue; and
an artificial or allograft or xenograft chord;
the chord extending between a first and a second end, the first and second ends being secured to the distal implant part, and the chord extending from the distal implant part to the proximal implant part and back to the distal implant part and being looped through the proximal implant part;
wherein the distal implant part and the proximal implant part are arranged in the lumen of the implant delivery device axially next to one another for being released sequentially, with the distal implant part being distally of the proximal implant part;
and wherein a portion of the chord between the first and second ends is stored proximally of the proximal implant part in the implant delivery device.

10. The medical device according to claim 9, wherein the distal implant part comprises a self-spreading portion spreading radially outside when the distal implant part is released from the lumen, the self-spreading portion being capable of anchoring the distal implant part in the tissue.

11. The medical device according to claim 9, wherein the proximal implant part comprises a self-spreading portion spreading radially outside when the proximal implant part is released from the lumen.

12. The medical device according to claim 9, wherein the chord is displaceable relative to the proximal implant part by a sliding movement that centers the proximal implant part relative to the chord when the proximal implant part implant is subject to a pulling force relative to the distal implant part.

13. The medical device according to claim 9, wherein the distal implant part comprises a shaft portion and a plurality of legs, wherein the shaft portion and the legs both extend proximally from a distal head, wherein in a released state the legs are bent radially outwardly away from the shaft portion, and wherein the first and second ends of the chord each run through the shaft portion from a proximal portion thereof to a distal portion thereof and are fixed relative to the distal portion.

14. The medical device according to claim 13, wherein the chord is fixed at the distal end of the shaft by a knot.

15. The medical device according to claim 9, wherein the proximal implant part is configured to lie flat on a leaflet surface with two portions of the chord, each having one of the ends, extending from the proximal implant part through the leaflet tissue and through the ventricle to the distal implant part.

16. The medical device according to claim 9, wherein the proximal implant part is coupled to the chord in a manner that a pulling force on the chord does not transmit any torque on the proximal implant part lying flat on the leaflet.

17. The medical device according to claim 9, wherein in a non-released state the proximal implant part in cross section has the shape of a circular segment.

* * * * *